(12) United States Patent
Schmidt et al.

(10) Patent No.: US 6,839,678 B1
(45) Date of Patent: Jan. 4, 2005

(54) COMPUTERIZED SYSTEM FOR CONDUCTING MEDICAL STUDIES

(75) Inventors: Volker Schmidt, Erlangen (DE); Werner Striebel, Lauf (DE)

(73) Assignee: Siemens Aktiengesellschaft, Münich (DE)

( * ) Notice: Subject to any disclaimer, the term of this patent is extended or adjusted under 35 U.S.C. 154(b) by 0 days.

(21) Appl. No.: 09/247,919

(22) Filed: Feb. 11, 1999

(30) Foreign Application Priority Data

Feb. 11, 1998 (DE) ......................................... 198 05 535

(51) Int. Cl.[7] .......................... G06F 17/60; G08B 5/22
(52) U.S. Cl. ............................................. 705/3; 705/2
(58) Field of Search ...................... 705/2, 3; 600/300; 707/104.1, 10

(56) References Cited

U.S. PATENT DOCUMENTS

| | | | | |
|---|---|---|---|---|
| 5,655,084 | A | * | 8/1997 | Pinsky et al. ................... 705/3 |
| 5,991,731 | A | * | 11/1999 | Colon et al. .................... 705/3 |
| 6,209,004 | B1 | * | 3/2001 | Taylor ........................ 707/500 |

FOREIGN PATENT DOCUMENTS

EP         710 917 A1    *   5/1996

OTHER PUBLICATIONS de Groen et al., "Applying World Wide Web Technology to the Study of Patients with Rare Diseases" Annals of Internal Medicine, vol. 129, No. 2, p. 107–113, Jul. 15, 1998.*

Machlis, Sharon, "Web Database Helps Doctors Fight Cancer" ComputerWorld Oct. 12, 1998, p. 41–42.*

Papaconstantinou et al., "An Expert System for Assigning Patients into Clinical Trials Based on Bayesian Networks" Journal of Medical Systems, vol. 22, No. 3, p180–202 1998.*

* cited by examiner

Primary Examiner—M. Kemper
(74) Attorney, Agent, or Firm—Schiff Hardin LLP

(57) ABSTRACT

In a system for conducting medical studies a number of medical locations, such as clinics or medical practices, are connected to a central server via a computer network. The system is constructed in modular fashion, and it is automatically determined, with computer support within the system, whether a specific patient is eligible to participate in a medical study of the system, and if so, the sequence of the corresponding medical study is controlled centrally by corresponding modules, automatically and in a study-specific and patient-specific fashion.

21 Claims, 2 Drawing Sheets

COMPUTERIZED SYSTEM FOR CONDUCTING MEDICAL STUDIES

BACKGROUND OF THE INVENTION

1. Field of the Invention

The present invention relates to a computerized system for conducting medical studies.

2. Description of the Prior Art

Medical studies are usually conducted with the aid of patients who are in the care of medical practices or clinics. By means of such medical studies, the success of specific therapeutic measures and the like can be representatively evaluated by empirical inquiries. The medical studies in the clinics or medical practices are conducted on specific patients who satisfy prescribed inclusion criteria for the medical studies. The results of the medical studies are evaluated by study supervisors.

Medical studies, particularly multicenter studies, require a high administration and coordination outlay. Numerous problems must be overcome in conducting medical studies. The clinics and medical practices which participate in the medical study must be informed about the study to be conducted and the corresponding inclusion, or exclusion, criteria. Depending on these criteria, patients who are eligible for participation in the corresponding medical study must be identified or selected. The eligible patients must then be registered with the study supervisors and assigned to appropriate study groups. Finally, the data of the participating patients that are amassed in the course of a medical study must be correctly acquired and communicated to the study supervisors.

Heretofore, a majority of the administration work in the conduct of medical studies has occurred by human activity. A physician usually checks whether one of his or her patients is eligible for a specific medical study and reports this to the study supervisors, possibly via one or more intermediaries, the patient data usually being transmitted on paper. The study supervisors assign the patients to an appropriate group, create study protocols, monitor the prompt entry of study data and request missing data. The communication between the study supervisors and the medical practice or the participating patient usually occurs via conventional mail, i.e. by means of written correspondence.

It is obvious that this procedure demands a high administrative outlay and is time-intensive and expensive. In particular, the administrative outlay rises rapidly with the number of participating patients or participating clinics/medical practices.

Although proposals exist for an information system for conducting medical studies over the Internet or for supporting study supervisors by the use of computers, these are not sufficiently specific to provide a truly realizable tool for conducting a computer-supported study (cf. "Einsatz von Internet-Diensten und Werkzeugen zur Unterstützung der Dateneingabe und das Monitorings multizentrischer klinischer Studien", P. Wübbelt et al 42. Jahrestagung der GMDS, Ulm, September 1997, MMV Medizin Verlag München or "Ein WWW-basiertes Informations—und Kommunikationssystem für multizentrische medizinische Studien", A. Selz et al, Vortrag auf der 42. Jahrestagung der GMDS, Ulm, 1997).

SUMMARY OF THE INVENTION

It is an object of the present invention to provide a system for conducting medical studies which enables a simpler and more effective completion of medical studies.

The system according to the present invention is supported by computers. A number of clinics and/or medical practices which are available for participation in medical studies are connected to one another via a central server, on the basis of Internet technology, for example. This central server is responsible for the central administration of all medical studies currently being conducted, or which will be conducted, and in particular for the central control and monitoring of the studies being currently conducted. The inventive system is a modularly constructed EDP system, wherein the eligibility of a patient for one of the medical studies is automatically checked using a patient identification module employing existing data of that patient. If the patient is eligible, then the patient is automatically assigned to the corresponding medical study by the central server, and a study sequence module in the central server controls or monitors the sequence of the corresponding medical study centrally, by communication with the patient or the medical representatives responsible for the patient.

Medical practices of all specialties can be connected via the computer network, and a number of different patients can be reached, accordingly, so that sufficient numbers of patients for medical studies to be conducted can be quickly achieved with the inventive system. The treating physicians can report about their patients at the central server via a local computer which is allocated to the corresponding medical practice or clinic. By checking the corresponding patient data, it is automatically determined whether the respective patient is eligible for a specific medical study. If this is the case, the reporting physician obtains a short notification about the study outlay, the reimbursement, and so on. If the treating physician or the patient then agrees to participate in the medical study, additional information that is relevant to the performance of the medical study is communicated. Subsequent to the participation agreement, the study is conducted centrally by the server of the computer network using study software implemented in the server. In general, communication between the central study supervisors and the individual patients or physicians occurs via the computer network; i.e., the study is preferably conducted by communication of corresponding inquiries to the treating physicians or to the patients electronically.

Ambulatory medical practices and/or clinics are advantageously connected to the inventive computer network for conducting medical studies. This guarantees that the medical studies are conducted primarily in a setting such as that in which the majority of the doctor-patient contact takes place, which is also the setting in which a majority of practical medicine takes place. The high numbers of cases in the ambulatory field enable collectives or study groups to be compiled which can be easily compared with respect to age, multi-morbidity, etc. Due to the high volume of patients in the ambulatory sector, representative study volumes can be achieved quickly, and study results can be achieved quickly as well. Intermediate results thus can be extracted at any time during the course of the corresponding study via the computer network without complications. By querying a number of clinics/medical practices of a variety of specialties, a plurality of patients can be entered into the medical studies, and high-quality studies accordingly can be conducted relatively quickly. Due to the networking of the central server with the individual local computers, which are allocated respectively to specific medical locations (medical practice, clinic, etc.), the organizational outlay for the individual medical locations and for the patient is low.

Occasionally, in studies conducted at clinics, follow-up investigations of patients already released from the study are necessary. With the aid of the inventive system, these patients can be easily traced by the central server via the corresponding local computers of the medical locations responsible for the respective patients, and they can be queried even after release from the medical study. These patients thus are not lost to the clinic.

DESCRIPTION OF THE PREFERRED EMBODIMENTS

Figure 1:
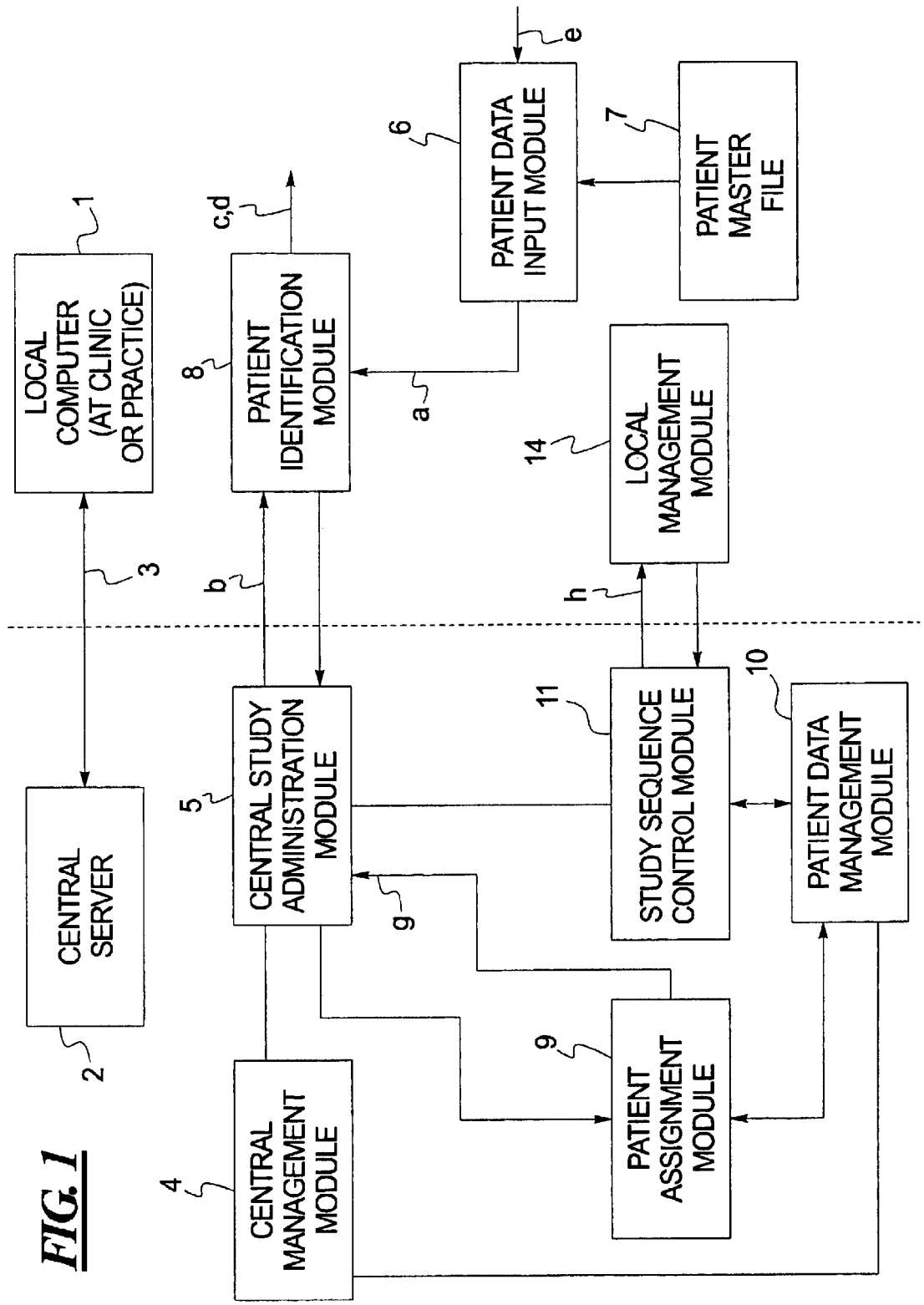
FIG. 1 a simplified block diagram of a first exemplary embodiment of the inventive system for conducting medical studies.

As depicted in FIG. 1, a number of local computers (for simplification only one local computer is shown) are connected to a central server 2. The central server 2 can be connected to each local computer 1, in analog or digital (ISDN) fashion, via the conventional telephone network, for example. The communication between the central server 2 and each local computer 1 can occur via the Internet. Each local computer 1 is allocated to a specific medical location, such as a medical practice or a clinic, which is provided for participation in medical studies that are conducted by the central server 2.

The inventive system is modularly constructed; i.e., specific modules are implemented in the central server 2 as well as in the local computer 1. These modules, in combination, assure a smooth sequence of the individual medical studies.

A central study administration module 5 is implemented in the central server 2. This study administration module 5 manages and stores central information about all the medical studies which are currently being conducted, or which will be conducted; i.e., all the medical studies conducted via the computer network are centrally administered by this study administration module 5. Accordingly, this central study administration module 5 also permits each individual medical study to be defined, i.e. specification of the study sequence. The specific inclusion or exclusion criteria for each medical study are stored in this study administration module 5. Furthermore, additional information which is required for the completion of each individual study is stored, such as the planned and achieved scope (number of participants) of each medical study, or which control investigations or therapeutic measures should take place at what time.

A central module 4 for managing all the medical locations which are authorized to participate in medical studies is also provided in the central server 2. This module 4 manages information about the individual physicians, clinics, or practices which are provided for participation in medical studies. The information stored in the central modules 4 and 5 serves as a basis for communication between the central server 2 and each local computer 1 which is connected to the computer network and respectively allocated to a specific medical location.

Besides these two central modules of the central server 2, other modules are implemented in the central server 2, the function of which is explained below with reference to the modules of the individual local computers 1.

So that an evaluation can be made as to the eligibility of a specific patient for a medical study of the system, and so that the patient can be assigned to this medical study, as warranted, there must first exist corresponding patient data which identify and sufficiently describe the respective patient. A patient data input module 6, which is implemented on each local computer 1, serves this purpose. This module 6 serves for the input/management of data of those patients who are treated by the corresponding medical location of the respective local computer 1. A variety of solutions are possible for the entry of the patient data. For example, the module 6 can be implemented as an independent Internet service; i.e., the corresponding patient data of each individual patient are entered and checked by the treating doctor individually, in addition to the already existing system of the clinic or medical practice. This input can occur by means of a telephone query, whereby a questioner extracts the necessary patient data from the patient by a series of appropriate questions and records the answers at the corresponding medical location. These questions could also be conducted with support by a computer system, whereby the entry of the patient data can occur in the corresponding medical location via telephone keyboard. This option guarantees that only the patient data which are actually required for the study are entered and transmitted. As depicted in FIG. 1, however, the patient data input module 6 also can be coupled with the data processing taking place at the corresponding medical location, i.e. with the already existing patient master file 7 of the respective medical location, so that new patients/diagnoses can be automatically acquired locally by the patient data input module 6 and can be transmitted to the central server 2, via the Internet, for example. In this case, a treating physician would automatically receive an acknowledgment or feedback as to which of his or her patients is/are eligible for a medical study that is conducted by the system, without having to enter additional patient data.

The patient data acquired by the module 6 are checked by a patient identification module 8 (cf. connection a). For each incoming set of patient information, this patient identification module 8 checks if the corresponding patient is eligible for currently running or future studies of the system for which patients are still needed. For this purpose, the patient identification module 8 accesses the study information of the individual studies, which is stored in the central study administration module 5 of the central server 2 (cf. connection b), and, using the study information thus obtained, the module 8 checks whether the corresponding patient satisfies the inclusion criteria of the respective studies, and whether the patient is already a participant of the respective studies. If the patient data available to the patient identification module 8 are not yet sufficient for a reliable evaluation, a corresponding request or acknowledgment is automatically transmitted to the treating physician by the patient identification module 8 (cf. output c). This request can occur in the form of a computer message displayed at the local computer 1 of the responsible medical location, for example. If, with the aid of the available patient data and of the study information delivered by the central study administration module 5, the patient identification module 8 has determined that the corresponding patient is eligible for one of the studies, then the medical location which entered the data automatically receives a query (e.g. via E-mail, Internet or fax) as to whether the treating doctor and the corresponding patient willing to participate in the study (cf. output d). Documents that are necessary for participation, such as a Declaration of Consent, can be automatically sent to the responsible medical location, or printed by the appertaining local computer 1.

The responsible physician or the patient in question can then confirm and consent to participation in the proposed study by a corresponding message. This can occur in the form of an input at the appertaining local computer 1 of the medical location, in particular (cf. input e).

When the patient's Declaration of Participation is recorded, then the patient is enrolled in the proposed medical study and the patient data are finally made available to the central server 2 (cf. connection f). In the exemplary embodiment depicted in FIG. 1, a patient identification module 8 is implemented at each local computer 1. This guarantees that unnecessary patient data are not transmitted to the central server 2, though the corresponding patient has not yet confirmed his or her participation in the proposed medical study.

Subsequent to the Declaration of Participation of the treating physician and of the participating patient, the patient data and other required information, such as relates to the treating physician, for example, is allocated to a patient assignment module 9. This module 9 assures that a patient who is participating in a medical study is assigned to a corresponding study group for this study. The assignment preferably is made such that optimally comparable and equally informative study groups are created by the patient assignment module 9. To this end, the patient assignment module 9 accesses the data of an additional centrally implemented patient data management module 10, in which all the data of all the patients who are participating in the individual medical studies are managed in a study-specific fashion. In this way, the patient assignment module 9 can assign a patient to a study group automatically, in consideration of the other participants of the study in question.

Once the patient is assigned to a study group of the medical study by the patient assignment module 9, an automatic updating of the study data stored in the central study administration module 5 occurs by a corresponding message (cf message g), particularly in order to bring the, information in the module 5 relating to the number of participants of the corresponding study fully up to date.

As already explained, the patient data management module 10 serves for the central management of all the data of the patients participating in the individual studies of the system. In particular, this module 10 serves for the study-specific and patient-specific management of the data, of the individual participants, which are amassed in the framework of the respective studies.

The study sequence control module 11, which is also implemented in the central server 2, is ultimately of central importance. This. module 11 is responsible for the control, or monitoring of the study sequence of each individual patient. To this end, the study sequence control module 11 accesses the information about the individual studies, which is stored in the central study administration module 5, as well as accessing the patient data of the individual patients, which are stored in the patient data management module 10, in order to determine, at any given time, and in a study-specific and patient-specific fashion, with the aid of the study description data and of the patient data, which measures should currently be taken with the individual participants or patients.

For each patient depending on the study and the time, queries or messages are automatically sent by this study sequence control module 11 to the treating medical locations or directly to the patient, these queries or messages containing information about which control investigations or therapeutic measures should be undertaken next (cf. output h).

These messages or queries can be transmitted by the central server 2 to the responsible medical location by telefax by example. Since the central server 2 is connected to the individual local computers 1 of the medical locations via the computer network 3 anyway, however, transmittal of this information via an electronic path (e.g. per E-mail, Internet, etc.) is advantageous. A local management module 14 can be implemented on each local computer 1, this module 14 managing and printing out the incoming queries or messages of the central study sequence control module 11.

The messages sent by the study sequence control module 11 usually require corresponding acknowledgments or feedback on the part of the responsible medical location giving information about the result of the control investigations or therapeutic measures to be carried out, it being possible for the central server 2 to use these acknowledgments for the evaluation of the corresponding medical study. In principle, these acknowledgments can be transmitted on the same path as the messages of the study sequence control module 11 (cf. feedback e in FIG. 1). The study sequence control module 11 automatically monitors the input of the requested information and, given the failure to meet a specified deadline, for example, it automatically generates a reminder about the missing information to the responsible medical location as well as a corresponding notification of the study supervisors. Examination data which are obtained by the central study sequence control module 11 in the framework of medical studies by means of acknowledgments of the responsible medical locations are automatically stored in the patient data management module 10.

Figure 2:
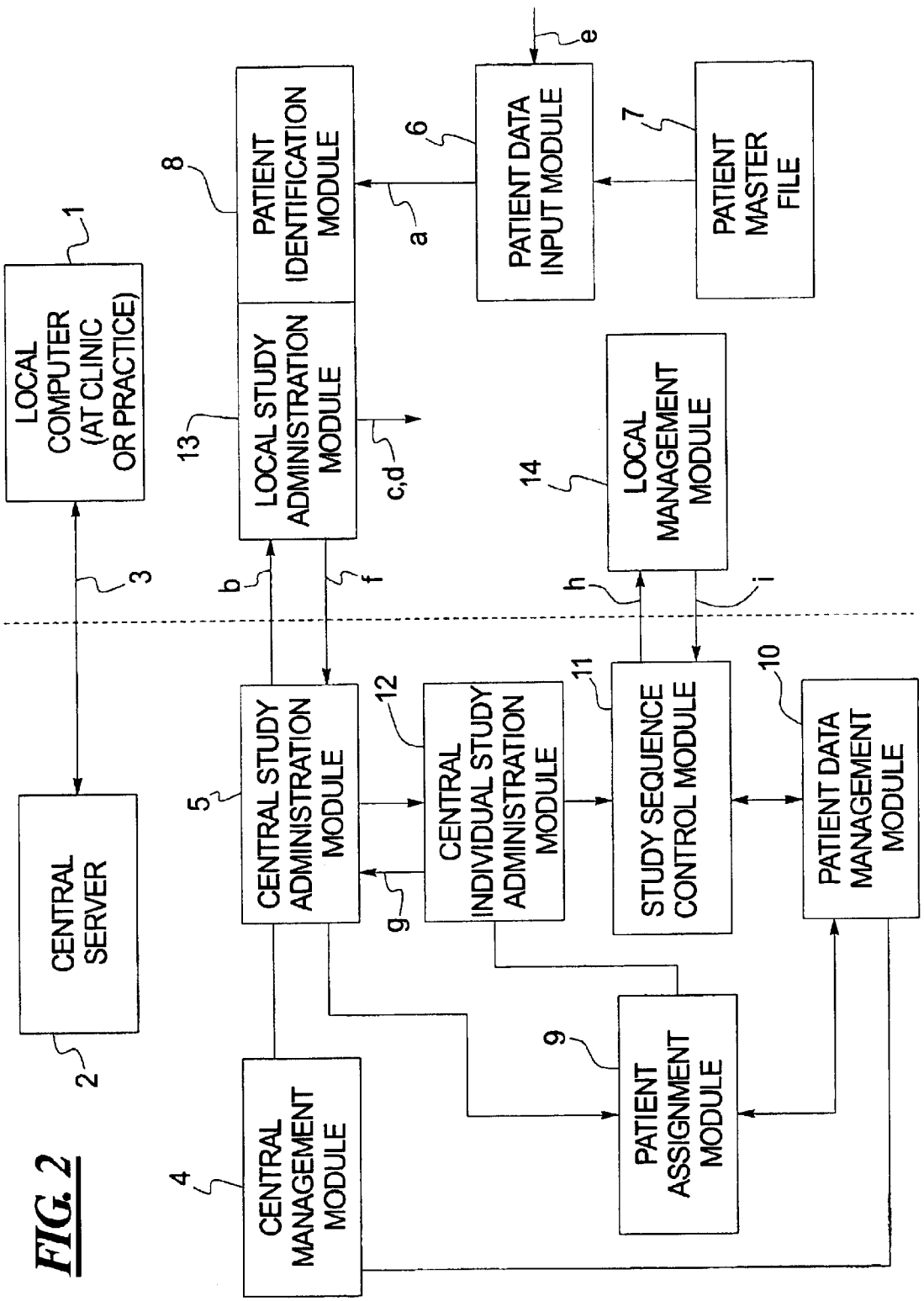
FIG. 2 a simplified block diagram of a second exemplary embodiment of the inventive system for conducting medical studies.

FIG. 2 depicts a second exemplary embodiment of the inventive system for conducting medical studies, whereby the system depicted in FIG. 2 generally corresponds to the system depicted in FIG. 1. In the embodiment of FIG. 2, however, a central individual study administration module 12 is additionally implemented in the central server 2, this module 12 serving as an interface between the patient assignment module 9 and the study sequence control module 11, as well as between the patient assignment module 9 and the central study administration module 5. Accordingly, this additional module 12 stores the data required for each individual medical study of the system, and, unifies functions which, in the exemplary embodiment according to FIG. 1, are conducted in part by the central study administration module 5 and the study sequence control module 11. Furthermore, according to FIG. 2, each patient identification module 8 is coupled with an optional local study administration module 13, which serves as an interface to the central study administration module 5 of the central server 2. This local study administration module 13 serves for the transmission of patient data between the corresponding local computer 1 and the central server 2 and takes over specific functions which are conducted by the patient identification module 8 in the exemplary embodiment depicted in FIG. 1.

The inventive system depicted in FIGS. 1 and 2 thus enables an automatic evaluation of existing patient data with respect to a possible inclusion in a medical study to be conducted by the system. The processing of the patient data occurs with computer support, and the study data of the individual participating patients are acquired automatically, whereby, depending on the existing information about the study to be conducted and the existing patient data of the participating patient, the system decides independently, with the aid of the study sequence control module 11, about the information to be gathered or the measures to be taken next. In sum, with the aid of the inventive system, not only are the acquisition and participation of a number of different patients in the medical study guaranteed, but also the study data obtained in the completion of the individual medical studies can be processed and evaluated extremely simply and without a large outlay for management technology.

Although modifications and changes may be suggested by those skilled in the art, it is the intention of the inventors to embody within the patent warranted hereon all changes and modifications as reasonably and properly come within the scope of their contribution to the art.

We claim as our invention:

1. A system for conducting medical studies comprising:
   a computer network;
   a plurality of local computers respectively disposed at medical locations available for participation in a medical study, each medical location having at least one patient associated therewith available for participation in a medical study, said at least one patient having patient data associated therewith accumulated prior to and independently of said medical study;
   a central server connecting said plurality of local computers to said computer network;
   a study administration module in said central server for managing all study information relating to current and future medical studies, said study administration module comprising a memory for storing study-specific study information, including a time sequence for each of said current and future medical studies, conditions for participation of a patient in each of said current and future medical studies, and a current number of participants in a current medical study;
   a patient identification module at each of said local computers for receiving said patient data and having access to said study information, for comparing said patient data to said study information for determining, isolated from said central server, whether the patient associated with the patient data is eligible for participation in a specific medical study among said current and future studies, said patient identification module automatically determining whether a specific patient is eligible for participation in said specific medical study using said patient data associated with said specific patient and said conditions for participation of a patient in said specific medical study stored in said memory in said study administration module and, if said specific patient is eligible, for automatically conducting a procedure to obtain consent of said specific patient for said participation and, only if said consent is obtained, communicating said patient data associated with said specific patient to said study administration module; and
   a study sequence control module in said central server which is informed of said eligibility and said patient data of said specific patient by said study administration module, for controlling a sequence of a study for which the specific patient is eligible by communicating with the medical location with which the specific patient is associated via the local computer at the medical location, and for gathering study data from the specific patient.

2. A system as claimed in claim 1 wherein said computer network comprises a telephone network.

3. A system as claimed in claim 1 further comprising a location management module in said central server for managing information about all of said medical locations connected to the central server via the respective local computers.

4. A system as claimed in claim 1 further comprising a participant data management module in said central server for managing study-specific participant data of all patients participating in a medical study.

5. A system as claimed in claim 4 wherein said participant data management module includes a memory wherein data are stored, in patient-specific fashion, for all patients participating in a medical study, said data including said study data collected by said study sequence control module and supplied to said memory.

6. A system as claimed in claim 5 further comprising a patient assignment module in said central server for assigning a specific patient to a study group for a specific medical study, after said specific patient is determined to be eligible for said specific study by said patient identification module.

7. A system as claimed in claim 6 wherein said patient assignment module comprises means for, depending on participant data for patients already participating in said specific study, said participant being stored in said participant data management module, assigning a participating patient to said study group of said specific medical study for generating a plurality of study groups which are substantially comparable to each other.

8. A system as claimed in claim 1 further comprising a patient assignment module in said central server for assigning a specific patient to a study group for a specific medical study, after said specific patient is determined to be eligible for said specific study by said patient identification module.

9. A system as claimed in claim 1 wherein said patient identification module employs the determination of whether said specific patient is eligible for participation in a specific medical study as a first criteria, and additionally determines whether said specific patient is already participating in said specific medical study as a second criterion and, if said first and second criteria are met, informs said study administration module of said eligibility.

10. A system as claimed in claim 1 wherein said patient identification module comprises means for emitting an error message if said patient data are insufficient for evaluating whether said patient is eligible to participate in one of said medical studies.

11. A system as claimed in claim 1 further comprising, at each of said local computers, a patient data input module for entering and managing said patient data for said at least one patient associated with the medical location at which said local computer is disposed.

12. A system as claimed in claim 1 further comprising, at each of said local computers, a patient master file identifying all patients associated with said medical location, and wherein said patient data module is connected to said patient master file and comprises means for automatically reading patient data from said patient master file for making the data from said patient master file available to said patient identification module.

13. A system as claimed in claim 11 wherein said patient data input module comprises means for entering patient data into a memory in said patient data input module as said patient data become available.

14. A system as claimed in claim 13 wherein said patient data input module comprises means for entering patient data acquired via a telephone query with said patient.

15. A system as claimed in claim 14 wherein said patient data input module comprises means for entering data produced by a telephone keyboard.

16. A system as claimed in claim 1 wherein said study sequence control module comprises means for controlling a time sequence of a specific one of said studies for a specific patient using the patient data associated with said specific patient and the study information about said specific study.

17. A system as claimed in claim 1 wherein said study sequence control module comprises means for controlling a time sequence of each of said medical studies by generating messages to respective medical locations having patients associated therewith who are participants in one of said medical studies.

18. A system as claimed in claim 17 wherein said study sequence control module comprises means for automatically generating and transmitting said messages depending on a current status of one of said medical studies.

19. A system as claimed in claim 18 wherein said study sequence control module comprises means for transmitting said messages electronically via said computer network to said respective medical locations.

20. A system as claimed in claim 17 wherein said study sequence control module comprises means for monitoring feedback from said respective medical locations produced in response to said messages and, given an absence of feedback from a respective medical location, for generating an error message to the respective medical location from which feedback is absent.

21. A system as claimed in claim 1 wherein said study sequence control module controls only a specific one of said studies for said specific patient.

* * * * *